(12) United States Patent
Shennib

(10) Patent No.: US 8,688,189 B2
(45) Date of Patent: *Apr. 1, 2014

(54) PROGRAMMABLE ECG SENSOR PATCH

(76) Inventor: Adnan Shennib, Dublin, CA (US)

( * ) Notice: Subject to any disclaimer, the term of this patent is extended or adjusted under 35 U.S.C. 154(b) by 1962 days.

This patent is subject to a terminal disclaimer.

(21) Appl. No.: 11/131,574

(22) Filed: May 17, 2005

(65) Prior Publication Data

US 2006/0264767 A1 Nov. 23, 2006

(51) Int. Cl.
*A61B 5/0402* (2006.01)

(52) U.S. Cl.
USPC ............................ 600/382; 600/384; 600/386

(58) Field of Classification Search
USPC ......................... 600/382, 384, 386, 388–394
See application file for complete search history.

(56) References Cited

U.S. PATENT DOCUMENTS

| | | | |
|---|---|---|---|
| 3,547,107 A | 12/1970 | Gofman et al. | |
| 3,744,482 A * | 7/1973 | Kaufman et al. | 600/372 |
| 3,823,708 A | 7/1974 | Lawhorn | |
| 3,943,918 A | 3/1976 | Lewis | |
| 4,121,573 A | 10/1978 | Crovella et al. | |
| 4,233,987 A | 11/1980 | Feingold | |
| 4,666,441 A | 5/1987 | Andriola et al. | |
| 4,773,424 A | 9/1988 | Inoue et al. | |
| 4,781,200 A | 11/1988 | Baker | |
| 4,945,917 A | 8/1990 | Akselrod et al. | |
| 4,957,109 A | 9/1990 | Groeger et al. | |
| 4,967,761 A | 11/1990 | Nathanielsz | |
| 4,981,141 A | 1/1991 | Segalowitz | |
| 5,042,481 A | 8/1991 | Suzuki et al. | |
| 5,042,499 A | 8/1991 | Frank et al. | |
| 5,109,421 A | 4/1992 | Fox | |
| 5,123,420 A | 6/1992 | Paret | |
| 5,135,004 A | 8/1992 | Adams et al. | |
| 5,168,874 A | 12/1992 | Segalowitz | |
| 5,205,295 A * | 4/1993 | Del Mar et al. | 600/524 |
| 5,307,818 A | 5/1994 | Segalowitz | |
| 5,313,953 A | 5/1994 | Yomtov et al. | |
| 5,372,139 A | 12/1994 | Holls et al. | |
| 5,431,171 A | 7/1995 | Harrison et al. | |
| 5,443,072 A | 8/1995 | Kagan et al. | |
| 5,464,021 A | 11/1995 | Birnbaum | |
| 5,483,568 A | 1/1996 | Yano et al. | |
| 5,511,553 A | 4/1996 | Segalowitz | |
| 5,622,168 A * | 4/1997 | Keusch et al. | 600/391 |
| 5,634,468 A | 6/1997 | Platt et al. | |
| 5,678,562 A | 10/1997 | Sellers | |

(Continued)

FOREIGN PATENT DOCUMENTS

WO    WO 91/15995 A1    10/1999

OTHER PUBLICATIONS

American Heart Association, "Heart Disease and Strokes Statistics—2004 Update."

(Continued)

*Primary Examiner* — Tammie K Heller

(57) ABSTRACT

The invention provides a disposable programmable ECG sensor patch for the non-invasive detection of risk patterns according to programmed criteria. The patch is programmed by a medical professional to select one or more monitoring parameters for detection and alarm indication. One application is to detect changes in the ECG due to cardioactive drugs. Another application is triggering an alarm for a cardiac patient during a stress condition. The programmable patch operates in conjunction with an external programming unit for selecting the detection monitoring parameters.

21 Claims, 3 Drawing Sheets

(56) References Cited

U.S. PATENT DOCUMENTS

| | | |
|---|---|---|
| 5,724,025 A | 3/1998 | Tavori |
| 5,749,365 A | 5/1998 | Magill |
| 5,776,073 A | 7/1998 | Garfield et al. |
| 5,792,066 A | 8/1998 | Kwong |
| D407,159 S | 3/1999 | Roberg |
| 6,112,116 A | 8/2000 | Fischell et al. |
| 6,115,624 A | 9/2000 | Lewis et al. |
| 6,117,077 A | 9/2000 | Del Mar et al. |
| 6,128,526 A | 10/2000 | Stadler et al. |
| 6,134,466 A | 10/2000 | Rosenberg |
| 6,146,242 A | 11/2000 | Treur et al. |
| 6,169,913 B1 | 1/2001 | Hojaiban et al. |
| 6,171,256 B1 | 1/2001 | Joo et al. |
| 6,200,265 B1 | 3/2001 | Walsh et al. |
| 6,272,379 B1 | 8/2001 | Fischell et al. |
| 6,295,474 B1 * | 9/2001 | Munshi ............... 607/121 |
| 6,327,486 B1 | 12/2001 | Nissila et al. |
| 6,341,229 B1 | 1/2002 | Akiva |
| 6,385,473 B1 | 5/2002 | Haines et al. |
| 6,440,089 B1 | 8/2002 | Shine |
| 6,456,872 B1 | 9/2002 | Faisandier |
| 6,494,829 B1 | 12/2002 | New, Jr. et al. |
| 6,496,720 B1 | 12/2002 | Feild |
| 6,501,983 B1 | 12/2002 | Natarajan et al. |
| 6,524,239 B1 | 2/2003 | Reed et al. |
| 6,546,285 B1 * | 4/2003 | Owen et al. ............... 607/5 |
| 6,558,686 B1 * | 5/2003 | Darouiche ............ 424/423 |
| 6,572,636 B1 | 6/2003 | Hagen et al. |
| 6,580,947 B1 | 6/2003 | Thompson |
| 6,609,023 B1 | 8/2003 | Fischell et al. |
| 6,643,541 B2 | 11/2003 | Mok et al. |
| 6,658,284 B1 | 12/2003 | Rosen et al. |
| 6,690,959 B2 | 2/2004 | Thompson |
| 6,751,498 B1 | 6/2004 | Greenberg et al. |
| 6,775,566 B2 | 8/2004 | Nissila |
| 7,206,630 B1 | 4/2007 | Tarler |
| 2002/0003225 A1 | 1/2002 | Hampden-Smith et al. |
| 2002/0028991 A1 | 3/2002 | Thompson |
| 2002/0074311 A1 | 6/2002 | Funkenbush |
| 2002/0082491 A1 * | 6/2002 | Nissila ............... 600/391 |
| 2002/0193701 A1 | 12/2002 | Garfield et al. |
| 2003/0032988 A1 * | 2/2003 | Fincke ............... 607/5 |
| 2003/0069510 A1 | 4/2003 | Semter |
| 2003/0083559 A1 * | 5/2003 | Thompson ............ 600/372 |
| 2003/0149349 A1 | 8/2003 | Jensen |
| 2003/0212319 A1 | 11/2003 | Magill |
| 2004/0032957 A1 | 2/2004 | Mansy et al. |
| 2004/0229545 A1 | 11/2004 | Wolf |
| 2004/0260154 A1 | 12/2004 | Sidelnik et al. |
| 2005/0065557 A1 | 3/2005 | Powers et al. |
| 2005/0267376 A1 | 12/2005 | Marossero et al. |
| 2005/0277841 A1 | 12/2005 | Shennib |
| 2006/0030781 A1 | 2/2006 | Shennib |
| 2006/0047215 A1 | 3/2006 | Newman et al. |

OTHER PUBLICATIONS

Azad Khandaker, et al., "Fetal QRS Complex Detection from Abdominal ECG: A Fuzzy Approach," Engineering Multimedia University, Cyberjaya, Selangor, Malaysia.

Buhimschi, et al., "Electrical Activity of the human Uterus During Pregnancy as Recorded from the Abdominal Surface," 1997, Obstetrics and Gynecology, vol. 90, No. 102-111.

Kam, A..et al., "Detection of Fetal ECG with IIR Adaptive Filtering and Genetic Algorithms," 1999, Electrical and Computer Engineeering Department Ben-Gurion University, Beer-Sheva, Israel.

Kam A., et al., "Material ECG Elimination and Foetal ECG Detection—Comparision of Several Algorithms," 1998, Dept. of Electrical and Computer Engineering Department, Ben-Gurion University, Beer-Sheva, Israel.

Kanjilal, et al., "Fetal ECG Extraction from Signal Channel Maternal ECG Using SVD and SVR Spectrum," 1995, IEEE-EMBC and CMBEC.

Khalil, et al., "Detection and Classification in Uterine Electromyography by Multicale Representation," 1997, Proceedings—19th International Conf. IEEEEMBS.

Khamene, Ali, "A New Method for the Extraction of Fetal ECG from the Composite Abdominal Signal," Apr. 2000, IEEE Transaction of Biomedical Engineering, vol. 47, No. 4.

Manner et al., "Predicting Term and Preterm Delivery with Transabdominal Uterine Electromyogram," 2003, Obstetrics and Gynecology, vol. 101, No. 1254-1260.

Meyer, J.S. et al., "Sudden Arrhythmia Death Syndrome; Importance of the Long QT Syndrome," Aug. 2003, American Family Physician, vol. 68, No. 3, www.aafp/orig/afp.

Mochimaru, et al., "Detecting the Fetal Electrocardiogram by Wavelet Theory-Based Methods," Sep. 2002, Progress in Biomedical Research, vol. 7, No. 3.

Rudhakrishnan, et al., "A Fast Algorithm for Detecting Contractions in Uterine Electromyogram," Mar./Apr. 2000, IEEE Engineering in Medicine and Biology.

Soliman, G.M., et al., "Risk Stratification and Treatment for Sudden Cardiac Death," Cardiac Board Review Manual, Hospital Physician Board Review Manual, 2003.

Kanjilal, et al., Fetal ECG Extraction from Single Channel Maternal ECG, Jan. 1997, IEEE Transaction on Biommedical Engineering.

Kam et al., "Detection of Fetal ECG with IIR Adaptive Filtering," Mar. 1999, Proceedings ICASSP99, IEEE.

"Separation of Twins Fetal ECG by Means of Blind Source Seperation (BSS)," 2000, Proc. Of 21st IEEE Convention of the Electrical and Electronic Engineers in Isreal, Tel-Aviv.

* cited by examiner

PROGRAMMABLE ECG SENSOR PATCH

CROSS-REFERENCE TO RELATED APPLICATION

This application is related to co-pending patent application Ser. No. 10/913,586 and Ser. No. 10/913,166, each filed Aug. 5, 2004, and Ser. No. 11/095,821 filed Mar. 31, 2005, of the same applicant, each of which applications is incorporated by reference in its entirety herein. Applicant claims priority of the aforesaid applications with respect to common subject matter.

BACKGROUND OF THE INVENTION

A. Technical Field

This invention relates to the electrocardiogram (ECG), and, more particularly, to non-invasive monitoring and detection of risk patterns in the ECG attributable to medication or physical activity.

B. Prior Art

Cardiovascular diseases are pervasive, contributing to over 2.4 million deaths annually in the United States alone. Delay in recognition and treatment of a heart abnormality leads to more damage to the heart, higher cost of hospitalization and lower quality of life for the survivors.

Heart abnormalities typically develop over time and the risk of a heart attack can increase with adverse side effect of certain medications. Drugs affecting the heart, referred to herein collectively as cardioactive drugs, may be targeted for cardiovascular disease or other ailments not related to the heart. Anti-arrhythmia drugs are examples of drugs targeting the heart for the control of irregular heartbeats. Vioxx® and Celebrex®, which were widely prescribed for arthritis patients, are examples of cardioactive drugs not targeting the heart.

Pharmacological therapy represents the first line of defense for most cardiac abnormalities. For atrial fibrillation (AF), a common cardiac abnormality affecting millions of people, the medication can be targeted for slowing the conduction of electrical impulses, decreasing the excitability and automaticity of cardiac cells, or prolonging the refractory period of cardiac tissue. The effectiveness and tolerance of these medications are quite individualized. Medications are often changed in order to achieve the desired outcome of reducing symptomatic episodes of AF. To further complicate matters, some of these drugs can actually have the opposite effect causing the heart to become more irritable and setting the stage for new arrhythmias to occur.

Control of the ventricular rate due to AF is also important in that a prolonged rapid heart rate can cause permanent physiologic damage to the cardiac cells. These cells can undergo a form of "remodeling" that reduce the contractility of the heart muscle and cause cardiomyopathy to develop. It can be very challenging for the cardiologist to achieve adequate ventricular rate control in some patients. In such cases, the patient's heart rate may be well controlled with medication while at rest, but quickly exceeds the desired range as the patient becomes moderately active. Conversely, prescribed medication may control the patient's heart rate during activity but can cause the heart to slow excessively when the patient is at rest. Fine-tuning the medication regimen is important for reducing patient discomfort and minimizing adverse physiologic changes. Besides controlling heart rate, other medication can cause subtle changes in ECG patterns leading to arrhythmia and event heart attacks for certain individuals. ECG symptoms for increased cardiac risk include prolongation of QT interval and ST segment shifts.

By continuously monitoring the heart rate and detecting ECG patterns for an individual over time, the effects of cardioactive medication can be studied. Corrective measures can be taken prior to developing a serious cardiac condition. Unfortunately, continuous monitoring and detection of ECG risk patterns is not feasible with standard "resting ECG" instruments available in clinical setting. Visual observation of standard ECG charts is not likely to reveal trends and subtle changes in ECG patterns.

It is well known in the field of cardiovascular science, that a single ECG recording is often non-diagnostic for many individuals, including those with serious heart disease such as acute myocardial infarction. These individuals often exhibit "normal" ECG patterns, even during a cardiac episode. However, risk patterns can be revealed if the ECG is compared with previously recorded ECG patterns. Furthermore, certain individuals with an apparent abnormality in their ECG may actually have normal cardiac function if their ECG pattern is consistent over time. This is especially the case when age is considered in the diagnosis. For these and other reasons, differential ECG measurements taken over time with consecutive ECG readings are considered essential for the cardiac diagnosis of certain individuals. A differential measurement not only reveals variations in cardiac rhythms, but also shifts and trends in the ECG waveform patterns. Detection of these changes often requires the aid of a processor (a computer, a microprocessor or a digital signal processor). Using a processor, signal averaging techniques can be used to average a specific time window of the periodic ECG waveform for noise reduction and detection of ECG segment baseline shifts over time.

Microprocessor based ambulatory monitors have been developed to solve some the limitations of large hospital-based ECG instruments. For example, Holter monitors are portable ECG used mostly at home to monitor the ECG of an individual. These instruments typically use 5 or more ECG electrodes attached to the chest at one end and connected to a portable electronic device at the other end. The device is worn or strapped to the body for recording ECG signals in its memory. After 24 to 48 hours of continuous monitoring and recording, the Holter monitor is typically returned to the clinic, where the recorded ECG data is downloaded for review, record keeping, and for further analysis by clinicians.

Cardiac event monitors are similar to Holter monitors but generally smaller and have less memory for recording only a few minutes of ECG during a cardiac event. They are designed to detect an intermittent cardiac event, i.e. heart palpitation, dizziness, syncope, chest pain, etc. The looping memory event recorder is a more sophisticated version of an event recorder with a miniature electronic package attached to the patient's chest via two to three electrodes. Event monitors typically record a short segment of the ECG prior to activation by a switch. For example, when a patient experiences a palpitation, the device records the prior 45 seconds of ECG and also 15 seconds subsequent to switch activation. With this method of monitoring, transitory cardiac symptoms can be documented.

Although less bulky than Holter monitors, event recorders are also uncomfortable to wear and lack the diagnostic capabilities of Holter monitors. The ECG patches (electrodes) used with such prior art ECG monitors are disposable and replaced frequently for extended monitoring. However, the base unit of these instruments is reusable as it is "loaned" to patients by the clinic providing the diagnostic service.

The prior art instruments and methods discussed above, and others discussed below, fall short of providing inexpensive and comfortable means for detection of cardiac abnormalities and trends developing over time. Furthermore, prior art instruments do not provide the ability to select monitoring parameters and detection criteria, which need to be customized for the individual or a patient group. These settings often need to be individualized according to the age, cardiac condition, medication used and the activity level permitted for the individual.

U.S. patent application serial no. 2003/0069510 to Semler discloses a disposable vital signs monitor that is a "flexible, nominally flat planar form having integral gel electrodes, a sticky-back rear surface, an internal flex circuit capable of sensing, recording, and play out several minutes of the most recently acquired ECG waveform data and a front surface that includes an output port preferably having one or more snap connectors compatible with lead harness . . . ." The monitor is designed for short-term monitoring as stated: "a relatively short term battery life, as it is intended for limited-term use." Semler's invention is primarily an ECG recorder and it is neither programmable nor designed to detect ECG risk patterns intrinsically. This and other limitations as disclosed exclude Semler's invention for conveniently monitoring the effect of medications or stresses on the heart, particularly in home settings.

U.S. Pat. No. 5,634,468 to Platt et al. discloses a sensor patch for obtaining physiologic data, including temperature, and transmitting a conditioned signal to a portable unit nearby and subsequently to remote monitoring equipment. Platt's patch neither saves ECG data nor performs analysis. For these purposes, it relies on external devices.

Recent publicity regarding adverse effects of certain medications highlights the need for more effective means of monitoring the effects of cardioactive drugs, including during clinical trials prior to regulatory approval. Using existing instruments to continuously monitor the ECG for a large patient population over an extended period of time is extremely costly and prohibitive in most cases.

Another problem with current heart monitoring is related to implant pacemakers and defibrillators. These programmable implant devices sometimes fail to properly deliver the necessary stimuli to the heart due to variety of reasons including incorrect device programming or improper lead attachment. Providing non-invasive ECG monitoring with selectable criteria for monitoring and setting off an alarm is highly desirable for millions of implant wearers, particularly new users.

A major objective of this invention is to provide an inexpensive non-invasive device and method to monitor the effect of drugs over an extended period of time. This device must be convenient, unobtrusive with minimal impact on the lifestyle of the user to ensure compliance with long term monitoring.

Another objective of this invention is to provide a highly miniaturized body-worn ECG monitor for automatically detecting subtle cardiac shifts.

Furthermore, a major objective is to provide ECG monitoring with means for individually selecting the monitoring mode, detection parameters and alarm criteria.

Another objective is to provide a programmable ECG sensor with automatic detection and alarm for alerting the patient to a cardiac stress condition according to programmed criteria.

SUMMARY OF THE INVENTION

The invention provides a disposable programmable sensor patch for the non-invasive detection of cardiac risk patterns according to programmable criteria. The smart patch monitors surface electrocardiogram (ECG) and selectively records cardiac events and ECG risk patterns according to the programmed parameters. The self-adhered patch is placed on the torso and preferably the chest area near the heart for sensing and analyzing the ECG.

The patch comprises a microprocessor, battery, two or more ECG electrodes, ECG amplifier, and analog-to-digital converter for converting ECG signals to digital data for numeric computations by the microprocessor. The patch also incorporates a wireless receiver for receiving wireless programming signals from an external programming device. An alarm is optionally incorporated to alert the user or others nearby when a risk condition is detected. The patch is programmed to detect a specific risk pattern in the ECG of an individual.

In one application, the patch detects subtle changes in the ECG pattern due to a cardioactive drug being evaluated. The medication dosage can then be verified, modified, or an alternate medication is suggested. In another application, alarm parameters are selected and programmed by a physician to trigger the built-in alarm during a stress condition such as exercise. Yet another application is monitoring non-invasively the function of an implant cardiac control device.

The programmable parameters include heart rate limits, ST segment position and shift, QT and QRS intervals, and pacing. Risk patterns generally relate to arrhythmia, syncope, myocardial infarction and transient ischemic attack. Once a risk pattern is detected, the corresponding ECG is automatically recorded for subsequent wireless transfer to a reporting device or the external programming device. A unique application of the invented patch is the ability to evaluate new and experimental drugs with convenience and minimal cost to the patient, the pharmaceutical company and the healthcare system. The duty cycle of the monitoring operation can be programmed from continuous mode to periodic monitoring to reduce power consumption and achieve extended monitoring. The software-based programmer, which may be a hand-held device or PC-based instrument, comprises a display panel for showing the programmable options and the estimated life of the patch based on the selected parameters.

BRIEF DESCRIPTION OF THE DRAWINGS

The above and other aims, objectives, aspects, features and advantages of the invention will be better understood from a consideration of the following detailed description of the best mode contemplated for practicing the invention, taken with reference to certain preferred embodiments and methods, and the accompanying drawings in which.

DETAILED DESCRIPTION OF THE PRESENTLY CONTEMPLATED BEST MODE OF PRACTICING THE INVENTION

The invention, shown in various embodiments of FIGS. 1-6 is a disposable programmable patch for non-invasive detection of ECG risk patterns according to programmed criteria. The patch 10 is thin, flat, and flexible for placement on the upper body of a person whose heart is being examined. The sensor patch relies on surface electrocardiogram (ECG) for detecting changes and trends in the ECG according to the programmed monitoring parameters. An application of particular interest is monitoring the performance of cardioactive drugs and assessing the regimen or safety of the medication. These drugs can be targeted for cardiac disease or non-cardiac ailments with possible cardiac risks. A related application is for obtaining safety and efficacy data for pharmaceutical films seeking regulatory approvals for their new or experimental drugs. Another application is programming heart rate limits for a cardiac patient during stress or exercise. For example, a cardiac patient can be given the invented patch programmed to alert for the occurrence of risk patterns in the ECG. An alarm transducer, integrated within the patch, may be of any suitable form for perception by the cardiac patient including a buzzer, visible light indicator or vibratory transducer.

The smart patch of the present invention is fully self-contained and self-powered. In the application of drug monitoring, the patch analyzes the ECG for an extended period of time spanning one or more weeks. The physician, clinician or medical researcher selects monitoring and detection parameters, referred to here generally as parameters, which are programmed into the patch according to the individual being evaluated or the individual group being studied. For example, a patient at risk of certain type of arrhythmia may be monitored specifically to detect premature atrial contractions (PAC). Others may be monitored for changes, in absolute or relative terms, in ECG segments such as ST segment shifts or QT interval.

Figure 1:
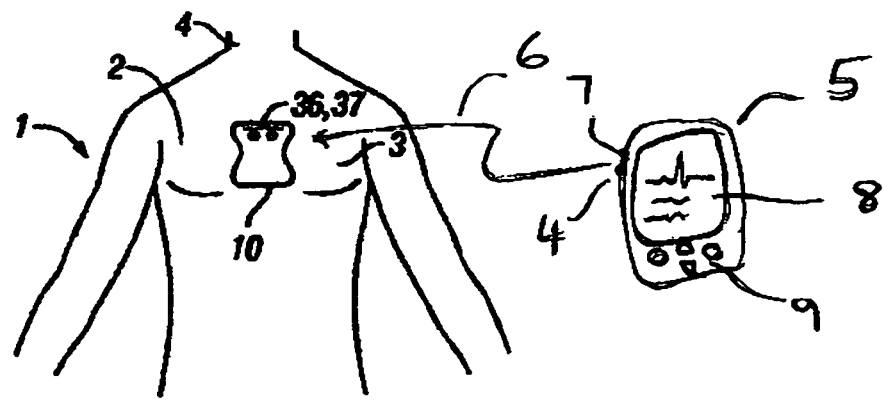
FIG. 1 is a view of the cardiac test patch programmed wirelessly by a hand-held programming device.

Referring to the embodiment of FIG. 1, the programmable sensor patch 10 is programmed by an external handheld programmer 5, which communicates wirelessly and sends wireless commands via wireless signals 6. The sensor patch 10 comprises wireless sensor element shown as an infrared transceiver 37 which receives wireless signals 6 sent by wireless transmitter 7 shown as light emitting diode (LED) incorporated in programmer 5. The programming parameters are selected by keypad 9 and displayed on the display unit 8 of the programmer 5. For bi-directional wireless transmission, wireless signals are transmitted from infrared transceiver 37 within patch 10 to optical detector 4 within hand held programmer 5.

Figure 2:
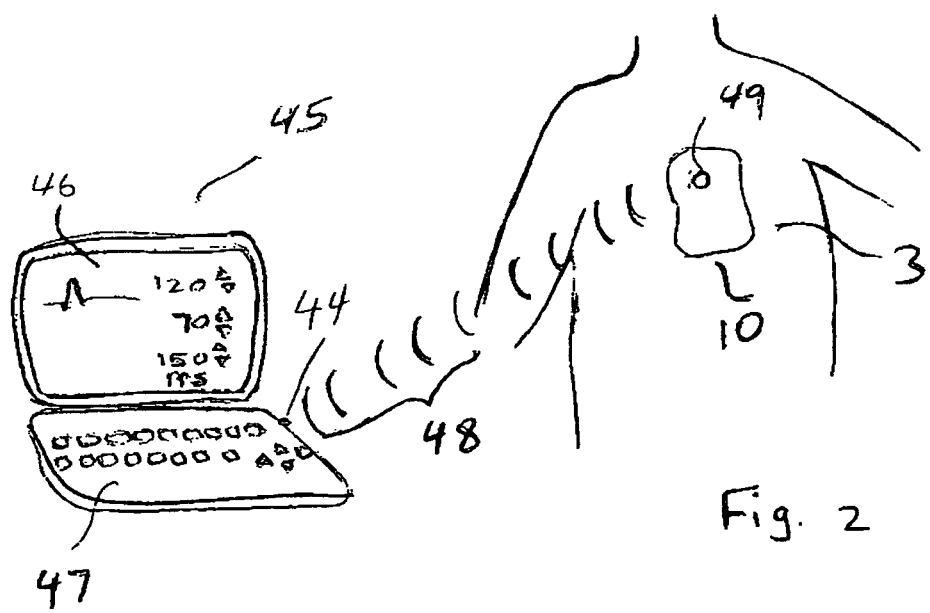
FIG. 2 is a view of the cardiac test patch programmed wirelessly by a PC-based programming device.

Referring to an alternate embodiment of FIG. 2, the patch programmer 45 is a personal computer (PC) communicating wirelessly via radio frequency (RF) signals 48 to send programmable parameters to programmable patch 10. The patch incorporates an RF wireless antenna 49 and receiver circuit (not shown) for achieving wireless communications to and from PC programmer 45 via its RF transceiver port 44. The transceiver port 44 is alternatively provided in plug-in interface device (not shown). Similarly, monitoring and detection parameters are selected using keypad 47 and display 46.

Figure 3:
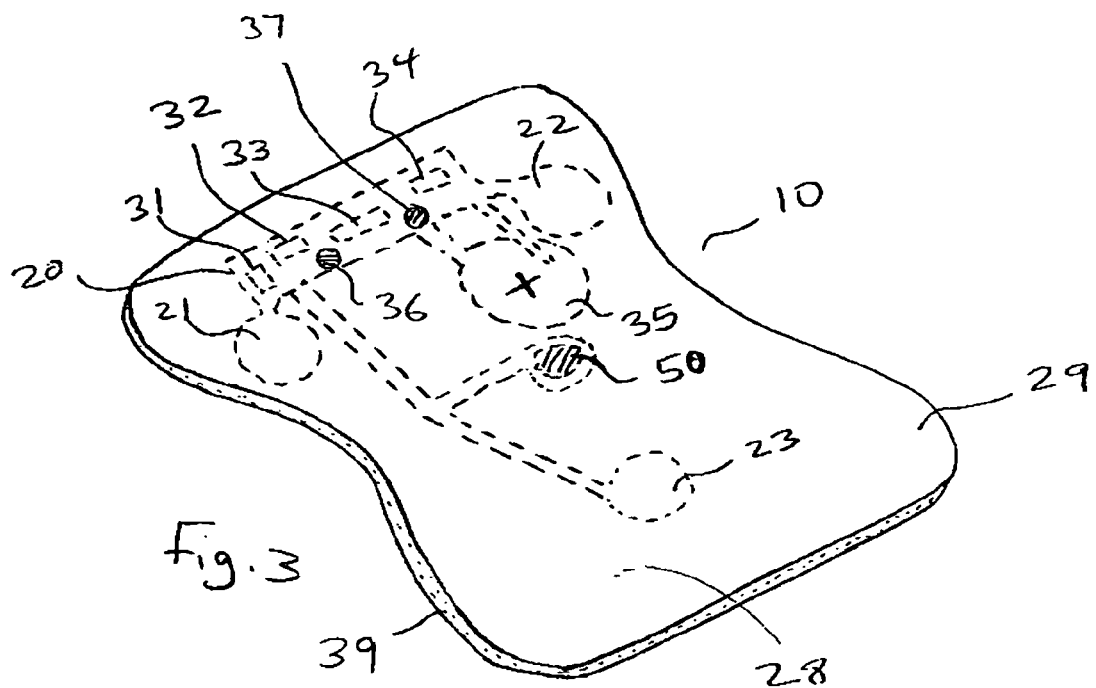
FIG. 3 is a top view of the cardiac test patch having 3 electrodes, flexible circuit, battery, and recording switch.

Referring to the embodiment of FIG. 3, the programmable sensor patch 10 comprises three ECG electrodes 21, 22, and 23, an ECG amplifier 31, a processor 33, and a battery 35. The processor 33 is typically a microprocessor or a digital signal processor for performing numerical computation on data obtained from an analog-to-digital converter 32. The sensor patch 10 also incorporates a memory 34, referring generally here to all types of solid-state memory for storage of program data, acquired ECG data and programmable parameters. A record switch 50 allows the user to manually record a cardiac event whenever felt.

The electronic assembly of the patch is formed of a flexible circuit substrate 20 with trace extensions to the electrodes 21, 22, 23, and to the battery 35. Conductive gel (not shown) covers the electrodes to conduct surface ECG potentials from the skin to the electrodes and subsequently to the ECG amplifier 31. The electrodes may be pre-gelled or alternately made for dry metal contact with electrodes directly contacting the skin. A non-conductive adhesive, i.e. Hydrogel, is preferably provided (not shown) at the skin contact surface for enhancing adhesion of the patch 10 to the skin. The patch 10 also comprises a thin substrate 28 for providing structural support. The substrate 28 is preferably made of soft flexible sheath material, such as polyurethane or cotton. The thickness of the patch device 10 (shown not to scale for clarity) is preferably in the range of 1.5 and 2.5 mm, but preferably no more than 3 mm for providing extremely low profile unobtrusive wear.

Non-conductive waterproof adhesive 39 present at the perimeter of the interior side of the patch prevents water entry and provides long term adhesion to the skin. The waterproof skin adhesive 39 prevents contamination of electrodes medially positioned thus maintaining long-term integrity of the skin-electrode electrical conductivity. This is important for providing long term function of the programmable patch while allowing the user to be exposed to water such as during bathing and swimming. The substrate 28, adhesive 39 and other materials used in the design of the patch are preferably air permeable in order to provide healthy air circulation to the skin and prevent moisture accumulation and contamination due to perspiration. Anti-microbial agents are preferably incorporated in the design of the invented patch, particularly in skin contact materials to prevent contamination of the patch and infection of the skin during an extended wear of the device. In the preferred embodiments, the patch is self-adhered. A porous and/or air permeable waterproof cover 29 protects the outer surface of the patch from external water exposure while allowing drying of the skin during perspiration.

Figure 4:
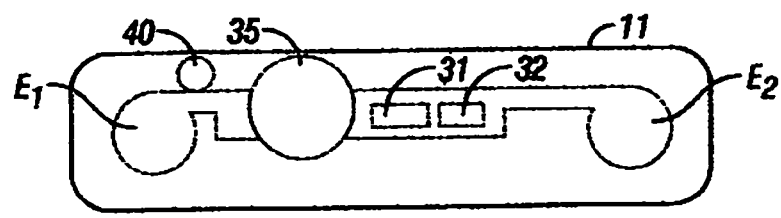
FIG. 4 shows a two-electrode band-shaped embodiment.

In the embodiments of FIG. 3, the programmable heart monitor patch 10 comprises three ECG electrodes for placement on the heart area 3 as shown in FIG. 1. The electrodes are arranged to provide a modified three-lead configuration with the electrodes 21, 22, 23 representing right arm (RA), left arm (LA) and left leg (LL) leads as in standard ECG instrumentation. This configuration results in lead measurements Lead-I, Lead-II, Lead-III. FIG. 4 shows a band-shaped patch 11 with a two-electrode embodiment, $E_1$ and $E_2$, for sensing the surface ECG. A wireless receiver 40 is provided to receive wireless commands from an external programmer as discussed above.

The invented patch is particularly suited to automatically detect cardiac events or subtle changes in the ECG waveform as per the criteria programmed into the patch. These risk patterns often elude conventional ECG instruments and monitoring methods spanning only a few minutes. Since the invented patch is waterproof and designed for continuous wear, even during showering and swimming, ECG changes and cardiac events are readily detected and recorded for documentation. Automatic detection and recording occurs by continuously monitoring and analyzing ECG data by the processor 33. Manual recording is optionally provided by a record switch 50 (FIG. 3), which is activated when the patient becomes aware of a cardiac episode. The activation of the switch 50 triggers a recording session of a predetermined length, for example 3 minutes prior to activation (pre-activation) plus 2 minutes post-activation. This method ensures detection and recording of even the most transient episodes.

Real-time ECG analysis provided by the invented patch allows for automatic detection of risk patterns that can lead to increased risk of a heart attack. These risk patterns are detected by comparing the characteristics of current ECG with prior ECG data according to the programmed limits. For example, shifts in certain segments of the ECG, such as the ST-segment, QT interval or QRS width, can be detected and recorded if any exceed the programmed limit. By recording mostly the risk patterns, rather than continuous ECG data, memory size requirement is minimal for a smaller more wearable patch device than conventional ambulatory monitors.

The detection of risk patterns and cardiac events can be indicated by an optional indicator. In the embodiment shown in FIGS. 1 and 3, a light emitting diode (LED) indicator 36 is provided. The indicator may be multi-colored to indicate different levels of risks. For example, a blinking green LED light can indicate a normal heart function while a red LED light indicates a risk condition. The LED can also be used to indicate proper patch operation.

Figure 5:
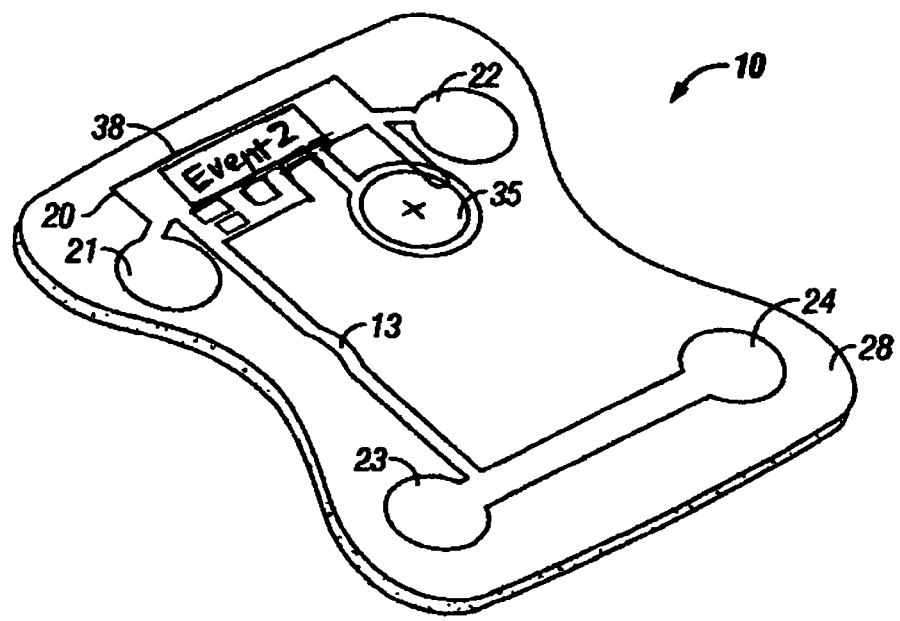
FIG. 5 shows an embodiment of the ECG patch with 4 electrodes and an LCD indicator.

Other possible forms of the indicator includes audible transducer such as a buzzer (not shown) or a speaker (not shown) and other visual types, such as a liquid crystal display (LCD) 38 as shown in FIG. 5. The advantage of an LCD indicator is to communicate more clearly the operation of the patch and condition detected. A key feature of the invention in all of its embodiments is integrating in a single low cost patch the combination of ECG analysis and risk detection. FIG. 5 shows a 4-electrode embodiment of the patch with fourth electrode 24 included. This and other electrode configurations are possible, as will become obvious to those skilled in the art of ECG measurements. Because the electrodes are integrated within the patch of the invention, motion artifact is significantly reduced when compared to standard ECG with separate electrodes and cabling. Furthermore, the integrated patch allows for inconspicuous, convenient long-term ambulatory applications.

Long-term signal processing by processor 33 is particularly suited for performing long term signal processing techniques such as signal averaging to enhance the details of the sensed ECG. Signal-averaged ECG involves the averaging of a large number of ECG periods, particularly for QRS, ST or QT segments, to remove noise artifacts and enhance the detection of small fluctuations over time.

The duty cycle and profile of the monitoring operation can be programmed from continuous monitoring to periodic sensing for prolonging battery life and extending patch operation. For example, the physician may program the patch to monitor the QT segment for only 3 minutes every hour and to record daily averages and limits. A summary report is then downloaded wirelessly. The operational life of the invented patch can be estimated and displayed by the programmer instrument based on programmed options selected, particularly the duty cycle profile, which largely determines the consumption rate.

Another application of the present invention is for monitoring the performance of implanted pacemakers and defibrillators. The invented patch can be programmed to monitor the proper activity of these implants to ensure correct device function and proper lead attachment. The patch can also be programmed to set off its alarm according to the alarm criteria programmed by the physician. This can be particularly beneficial for new implant users.

Figure 6:
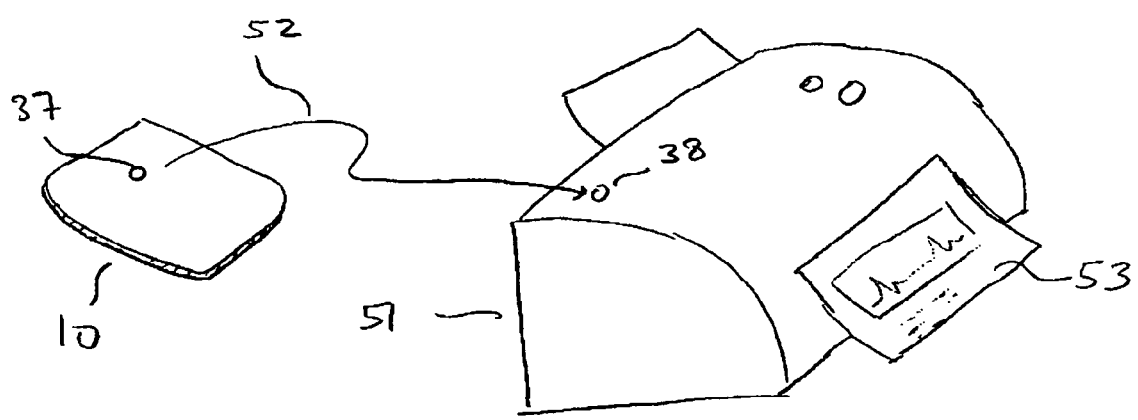
FIG. 6 shows optical transmission of a preformatted ECG report to a printer device.

A unique feature of the present invention is the wireless transmission of a preformatted report to a generic reporting device such as a printer or a wireless network. This allows for generation of a cardiac test report 53 without resorting to specialized instruments. FIG. 6 shows the invented patch 10 having an infrared transceiver 37 for sending infrared signal 52 to a printer 51 for printing a cardiac report 53. Many standard printers are equipped with wireless sensors and respond to standard wireless protocols, such as IrDA (Infrared Data Association). An optocoupler transceiver 37, incorporating an infrared LED and an optocoupler sensor, allows for bi-directional wireless communication with a reporting device. Similarly, using radio frequency (RF) transmitter (not shown), a report can be sent to a wireless printer or wireless network using standard RF protocols such as Bluetooth® and IEEE802®. With this method, the user or a clinician can place the patch in proximity to a wireless reporting device for obtaining a cardiac report 53. This report is generated internally by the processor 33 and sent wirelessly, either automatically when in proximity to a reporting device, or manually by activating a switch. For example by incorporating a reed-switch in the patch (not shown), which can be activated by a magnet placed in proximity to the patch when printing or reporting is desired.

The invented patch performs the analysis and formatting of results internally and sends the report directly to a generic printer or a generic network application such as Microsoft® Internet Explorer (Internet browser). In the later case, a report is wirelessly transmitted to the browser application by the invented patch. Once the report is loaded, it is then printed or relayed to a remote monitoring station via the Internet. An authentication screen is optionally transmitted prior to loading the personal data.

The ability to generate a cardiac report wirelessly and directly to a generic reporting device, as provided by the present invention, simplifies the delivery of cardiac monitoring information. For example, an individual under clinical investigation can wear the invented disposable programmable ECG patch and generate a daily report using a standard printer or standard wireless network. To ensure privacy and authentication of data, an access code can be provided with each patch for entering into an authentication screen prior to viewing or forwarding to a remote monitoring station. The present invention in this embodiment simplifies cardiac monitoring by eliminating the need for specialized instruments or training.

ECG data can also be sent to a remote location via standard trans-telephonic methods (not shown) whereby a telephone line adapter device can be used to translate ECG reports from the patch to the telephone line. The adapter unit can communicate wirelessly to the patch via infrared or RF signals and subsequently dial the reporting center and transmit the cardiac report to the monitoring station. The wireless transmission of cardiac data may be accomplished in numerous ways and methods known in the field of medical devices and wireless data transmission. This includes optical and RF means as shown above, magnetic, ultrasonic, and acoustic transmission. Inductive coupling through a coil (not shown) can also be used to transmit data, as well as for powering the patch externally during the transmission after depletion of battery power.

Although the invention is described herein with reference to preferred embodiments, one skilled in the art will readily appreciate that other applications may be substituted for those set forth herein without departing from the spirit and scope of the invention. Accordingly, the invention should only be limited by the claims included below.

The invention claimed is:

1. A disposable programmable cardiac test patch that performs non-invasive monitoring of a person's ECG, comprising:

a self adhering surface of said patch that secures said patch to a selected location on the body of said person;
a battery;
at least two electrodes that directly electrically contact the person's skin at said location and that receive surface ECG signals therefrom when said patch is secured at said location;
a waterproof adhesive that adheres said patch to said person's skin for long term wear thereon;
an amplifier electrically coupled to said electrodes for amplifying said received ECG signals;
a processor that is programmed to perform real-time ECG signal processing and further performs signal averaging of a periodic ECG segment for enhancing details of said received ECG signals to enable detection of subtle changes in said person's ECG signal pattern that result from said person taking a cardioactive medication;
a memory coupled to said processor for storing at least one programmable monitoring parameter for processing by said processor;
means for customizing said at least one programmable monitoring parameter to said person or to an individual group that is being monitored, said customization being performed by any of a physician, a clinician, or a medical researcher; and
means that receive a wireless programming signal, representing said at least one programmable monitoring parameter, from an external programming device and that load said wireless programming signal representing said at least one programmable monitoring parameter into said memory; and
a flexible, unitary substrate that incorporates said amplifier, said processor, said battery, said memory, and said electrodes into said patch;
wherein said patch has a thickness of less than 3.0 mm.

2. The programmable patch of claim 1 further comprising an indicator that indicates the occurrence of a detected risk pattern.

3. The programmable patch of claim 2, wherein said detection of a risk pattern includes measurement of ECG segment baseline and comparison with a prior ECG segment baseline.

4. The programmable patch of claim 1 further comprising means that wirelessly transmit cardiac data to an external reporting device via a wireless signal.

5. The programmable patch of claim 4, wherein said reporting device is a printer.

6. The programmable patch of claim 4, wherein said wireless signal includes any of infrared signal or radio frequency signal.

7. The programmable patch of claim 1 wherein said monitoring parameter represents any of heart rate, heart rate variability, arrhythmia, syncope episode, block, ECG segment position, ECG segment interval and monitoring duty cycle profile.

8. The programmable patch of claim 1 further comprising a switch that records a cardiac event felt by said person wearing said patch.

9. The programmable patch of claim 1, wherein said patch is waterproof and air-permeable for extended wear exceeding 7 days.

10. The programmable patch of claim 1, wherein said patch alerts a cardiac patient of a cardiac risk during physical activity including exercise.

11. The programmable patch of claim 1, wherein said patch monitors the performance of an implanted cardiac control device.

12. A disposable cardiac monitor patch for continuous wear on a selected location on the body of a person taking a cardioactive drug and that performs non-invasive monitoring of said person's ECG and evaluation of the cardiac effect of said cardioactive drug on said person, said patch comprising:
a waterproof self adhering surface of said patch that secures said patch to a selected location on the body of said person for long term wear thereon;
a battery;
at least two electrodes that directly electrically contact the person's skin at said location and that receive surface ECG signals therefrom when said patch is secured at said location;
an amplifier electrically coupled to said electrodes that amplifies said received ECG signals;
a processor that is programmed to respond to the amplified ECG signals that performs real-time ECG waveform processing and ECG waveform analysis of said amplified ECG signals, and that further performs signal averaging of periodic ECG segments for enhancing the details of said ECG signals to enable detection of a subtle changes in said person's ECG signal patterns according to at least one programmable monitoring parameter that is specifically selected and programmed for said person, or an individual group being evaluated; and
means for programming said at least one programmable monitoring parameter wirelessly into said processor by any of a physician, a clinician, or a medical researcher to detect changes in said person's ECG patterns resulting from said person taking said cardioactive drug.

13. The test patch of claim 12, further comprising means that receive a wireless programming signal from an external programming device to configure said at least one monitoring parameter for detecting changes in ECG patterns.

14. The test patch of claim 12 further comprising an indicator transducer that alerts to a detected risk pattern in the ECG.

15. The test patch of claim 12 further comprising means that record the ECG within memory integrated within said patch and that provide wireless playback of said recorded ECG.

16. The test patch of claim 12, wherein said processor is programmed to operate at a selected duty cycle profile.

17. A disposable programmable cardiac test patch that performs non-invasive ECG monitoring of a person who is implanted with a cardiac implant device, said patch comprising:
a waterproof self adhering surface of said patch that secures said patch to the chest area of said person for extended wear thereon of least one week;
an anti-microbial agent incorporated in the skin contact material of said cardiac patch to prevent contamination of the skin contact area and infection of the skin during said extended wear;
a battery;
at least two electrodes that directly electrically contact the person's skin at said chest area and that receive surface ECG signals directly therefrom when said patch is secured at said chest area;
an amplifier electrically coupled to said electrodes for amplifying said received ECG signals;
a processor that is programmed to respond to the amplified ECG signals and that detects a risk pattern according to at least one programmable monitoring parameter;

a memory coupled to said processor that stores programming for said processor and said at least one programmable monitoring parameter;

means for said at least one programmable parameter being selected and programmed into said memory by any of a physician, clinician, and a medical research according to the monitoring needs of said person or an individual group being monitored; and means that receive a wireless programming signal, representing said at least one programmable monitoring parameter, from an external programming device and that load said wireless programming signal into said memory.

18. A method of non-invasive cardiac monitoring of a person implanted with a cardiac control device, comprising the steps of:

a) applying a self-adhered cardiac patch comprising; two or more electrodes that directly electrically contact said person's skin surface and that receive a surface ECG signal directly therefrom; an amplifier that amplifies said ECG signals from said electrodes; a processor that is programmed to perform analysis of said amplified ECG signals; a memory that stores programming for said processor and at least one monitoring parameter;

b) selecting said at least one monitoring parameter by any of a physician, clinician, and a medical researcher according to the monitoring needs of said subject or an individual group being monitored;

c) sending a wireless programming signal, representing any of said at least one monitoring parameter, from an external programming device and loading thereof into said memory;

d) monitoring the ECG by said processor according to said at least one monitoring parameter;

e) detecting a risk pattern of the subject's ECG according to said at least one monitoring parameter.

19. The method of claim 18 further comprising the step of indicating a detected risk condition through an indicator integrated within said patch.

20. A device-implemented method of non-invasively monitoring the ECG signal of a subject with a device comprising a programmable patch adhered to the subject's body at a location suitable for said monitoring, comprising the steps of:

a) selecting one or more ECG monitoring parameters by any of a physician, clinician, or a medical researcher for programming into said programmable patch according to the monitoring need of said subject or an individual group being monitored;

b) storing said at least one or more ECG monitoring parameters in a programmable patch memory, wherein said one or more parameters is representative of a risk pattern in an ECG signal that is indicative of a cardiac effect of a cardiac drug on said subject;

c) performing signal averaging of periodic ECG segments and differential measurements of the ECG signal in said patch over an extended period of time; and d) detecting from said signal-averaged differential ECG measurements the occurrence of a risk pattern, according to said at least one stored ECG monitoring parameter.

21. The device-implemented method of claim 20, further including the step of indicating the occurrence of said detected risk pattern to at least one of said subject, a remote observer, and a remote recorder.

* * * * *